United States Patent
Sorenson

(10) Patent No.: US 6,311,134 B1
(45) Date of Patent: Oct. 30, 2001

(54) PROCESS AND APPARATUS FOR COMPARING CHEMICAL PRODUCTS

(75) Inventor: Matthew D. Sorenson, Easton, PA (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/247,058

(22) Filed: Feb. 9, 1999

(51) Int. Cl.$^7$ .................................................. G01N 11/00
(52) U.S. Cl. ............................ 702/22; 702/23; 702/27; 702/30; 702/31
(58) Field of Search .............................. 702/22, 23, 27, 702/30–32, 183, FOR 103, 104, 115–119, 134, 135, 170; 700/266, 90; 707/104; 426/231, 232; 705/29

(56) References Cited

U.S. PATENT DOCUMENTS

| | | | | |
|---|---|---|---|---|
| 4,736,316 | * | 4/1988 | Wallman | 364/149 |
| 4,750,133 | * | 6/1988 | Eiskamp et al. | 364/497 |
| 5,747,448 | * | 5/1998 | Ohyama et al. | 514/11 |
| 5,760,394 | * | 6/1998 | Welle | 250/303 |
| 5,978,804 | * | 11/1999 | Dietzman | 707/10 |
| 6,023,694 | * | 2/2000 | Kouchi et al. | 707/2 |
| 6,097,995 | * | 8/2000 | Tipton et al. | 700/266 |
| 6,144,897 | * | 11/2000 | Selliers | 700/269 |
| 6,163,732 | * | 12/2000 | Petke et al. | 700/106 |
| 6,185,506 | * | 2/2001 | Cramer et al. | 702/19 |
| 6,199,017 | * | 3/2001 | Tomonaga et al. | 702/19 |

* cited by examiner

Primary Examiner—Marc S. Hoff
Assistant Examiner—Carol S. Tsai
(74) Attorney, Agent, or Firm—Rothwell, Figg, Ernst & Manbeck

(57) ABSTRACT

A process and apparatus for comparing chemical products includes a plurality of multi-code groups. Each of the multi-code groups includes a substance code indicating a chemical substance code identifying the product, a specification number code indicating a number of specifications characterizing the chemical substance, and a specification type code indicating the types of specifications, if any, characterizing the chemical substance and/or the attributes, if any, of the chemical substance. The multi-code groups for different products are compared so as to identify similarities and differences between different products based on similarities and differences between corresponding substance codes, specification number codes and specification type codes of the different products.

21 Claims, 10 Drawing Sheets

Microfiche Appendix Included
(1 Microfiche, 18 Pages)

PROCESS AND APPARATUS FOR COMPARING CHEMICAL PRODUCTS

REFERENCE TO MICROFICHE APPENDIX

Submitted herewith is a microfiche appendix including a single microfiche having 18 frames.

BACKGROUND OF THE INVENTION

Users of various chemical products often have the need or desire to find alternative products made by multiple sources which are comparable to a known product. Various tools are available for cross-referencing known chemical products with related products. For example, printed tables are provided by various sources in which an individual can look up a chemical product number and find a related product of a different brand. These tables sometimes offer packaging information and size comparisons of the related products. Generally, they provide very little of the information necessary to make an educated decision regarding the available products. Many of the prior art printed tables are not current, and when combined with the limited nature of their comparison, this significantly undermines their credibility.

As an alternative to printed tables, E. M. Science provides a DOS-based computer program as well as an Internet website for cross-referencing chemical products. The E. M. Science programs appear to cross-reference products by linking a given product directly to another product (a one-to-one match), much like what is done by the printed tables. While these programs may save time, they still leave unaddressed the problem that very few chemical products are truly "equivalent" in every aspect. Moreover, any time either of the two products are changed, the equivalency of both products must be manually readdressed, and the one-to-one matching with each product likewise adjusted. The E. M. Science tools have limited credibility because they oftentimes fail to point out the critical differences in products.

As a result of these shortcomings in the above mentioned systems, there remains a need for improvements in cross-reference tools for chemical products.

BRIEF SUMMARY OF THE INVENTION

In accordance with the present invention, a process and apparatus for comparing chemical products utilizes a plurality of multi-code groups. Each multi-code group, associated with a particular chemical product, comprises a substance code indicating the chemical identification of the product, a specification number code indicating the number of specifications characterizing the chemical substance, and a specification type code indicating the known specifications or attributes of the chemical substance. The invention compares multi-code groups for different products so as to identify and convey the similarities and differences between various different products, based on similarities and differences between corresponding substance codes, specification number codes and specification type codes of the different products.

DETAILED DESCRIPTION OF THE INVENTION

Figure 1:
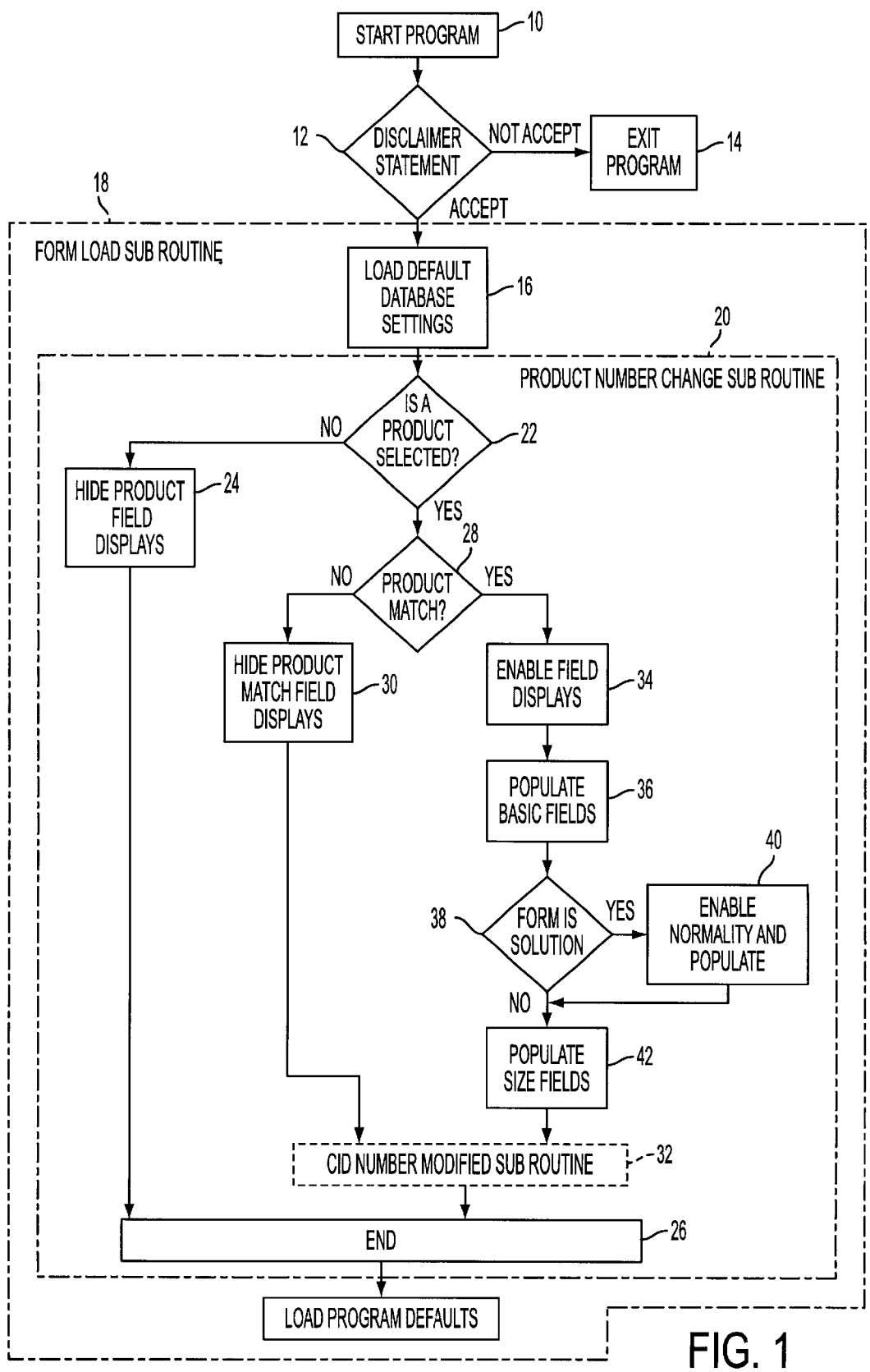
FIG. 1 is a block diagram illustrating a form load subroutine and product number change subroutine in accordance with one aspect of the present invention.

The present invention provides a tool for comparing chemical products which utilizes a plurality of multi-code groups. Each multi-code group characterizes a particular corresponding chemical product, and is comprised of several parts.

One part of the multi-code group is a substance code which identifies the primary chemical substance of the product. This substance code is also known as a chemical identification ("CID") number, or CID.

Another portion of each multi-code group is a specification number code, which indicates the number of known specifications or attributes characterizing the chemical substance.

A further portion of each multi-code group is a specification type code, which details the known specifications and attributes characterizing the chemical substance.

Typically, the specification type code indicates a plurality of specification types and/or a plurality of attributes of the corresponding chemical substance.

In preferred embodiments, the specification type code specifies all available product characteristics selected from the group consisting of product purity, moisture content, presence of one or more preservatives, presence of other ingredients, product sterility, suitable uses, compliance with established standards, and any combinations thereof. The specification type code can indicate of compliance with one or more standards established in compendial lists by the American Chemical Society, British Pharmacopeia, European Pharmacopeia, Japanese Pharmacopeia, Food Chemicals Codex, or the National Formulary. Additionally, the specification type code can indicate that the products carry one or more certifications by a government agency, such as the National Institute of Standards and Technology, identifying the product as, for example, a certified stain or solution. By way of further illustration, the specification type code may additionally indicate that the chemical product is specially tested and optimized for one or more particular applications such as in high pressure liquid chromatography, electronics, environmental related uses, liquid scintillation, spectrophotometry, or biotechnical synthesis. Furthermore, the specification type code may also indicate one or more certain attributes of the product which are of particular importance such as, for example, the product is cell culture tested, contains low water content, has no preservatives, has a particular preservatibe, is pyrogen tested, or is sterile.

In particularly preferred embodiments, each of the chemical products is furthermore described by one or more features such as the manufacturer's name, manufacturer's product number, manufacturer's description, manufacturer's grade, manufacturer's package suffix, product trade name, product package size, product package description and the like.

Most preferably, the chemical products are further described by their list price, discount price or both.

When cross-referencing products in accordance with the present invention, the multi-code groups for different products are compared so as to identify their similarities and differences. The corresponding substance codes, specification number codes and specification type codes of the different products are all considered to provide a complete comparison of the products.

The present invention also encompasses a machine comprising a data processing system including a plurality of multi-code groups as described above and a comparer device such as an algorithm which compares the multi-code groups in the manner described above.

The invention is further applicable to storage media including processing devices for storing a plurality of the multi-code groups as defined above and a comparer device capable of comparing the multi-code groups in the manner described above.

Such storage media may include one or more computer floppy disks, a CD-ROM, a computer hard drive, computer "flash" memory, computer hardware memory and the like.

In particularly preferred embodiments, the invention further comprises forming a database for comparing different chemical products by entering a product name, suffix, and number for each product into the database, selecting the features and characteristics corresponding to the product name from a menu containing a plurality of features and characteristics, and assigning a multi-code group to the product name corresponding to the selected features and characteristics.

The algorithm utilized by the program shown in the microfiche appendix compares the multi-code groups of different products and determines the degree of equivalence between the products. The program first looks for products that have the same substance code as the product in question and validates them as being the same basic chemical product. The specification number codes are then compared, and if the products have the same degree of characterization (i.e., the same specification number code) they are still considered equivalent and go to the specification type code check. If one product has more testing than another (i.e., differing specification number codes), the program indicates that on the program display. Finally, the specification type codes for the products are compared. If the specification type codes are identical, the products have equivalent types of testing and attributes. If the specification type codes are not identical, the program determines how they are different and displays the key attributes that are unique to each product. For any two products to ultimately be labelled "equivalent" they must have an exact match on all codes. Otherwise, the program will note and display any differentiation in degree or type of testing performed upon and the attributes possessed by the chemical products.

In accordance with one embodiment, all of the products which are displayed as alternatives to those originally entered include their current list prices. The user may enter into the program any product discounts given by the manufacturer, and such product discounts may be saved by the program. As the program searches for alternative products, and displays them, the program also displays the user's actual price on the screen and on any reports which may be generated.

In the exemplary embodiment, the invention is a Windows™ based system so that multiple programs can run simultaneously. Data can be printed in multiple report formats or exported electronically to other programs, such as a spread sheet, such that it may be further used or manipulated.

Updating the database in accordance with the invention is simplified since the multi-code group is all that needs to be updated. As long as the appropriate code is assigned to each product, the invention will supply the information necessary to adequately determine whether two products are equivalent for a given purpose. This cannot be achieved with any system which uses one-to-one mapping.

Utilization of the invention will be further described with respect to the drawings.

The drawings illustrate operations of various features of the embodiment of the invention as exemplified in the program disclosed in the microfiche appendix.

In FIG. 1A, program start 10 brings up a disclaimer statement 12 which, if not accepted, exits the program 14. If disclaimer 12 is accepted, default database settings are loaded in a form load subroutine 18.

In a product number change subroutine 20, an option 22 is provided for selection of a product. If no product is selected, the field displays are hidden 24 and the subroutine ends 26.

From step 22, if a product is selected, the program determines if a product match 28 is available. If no product match is available, field displays are hidden 30, and the program enters a CID number modified subroutine 32, described in greater detail below with respect to FIG. 3A. The CID number corresponds to the previously described substance code for a product.

If there is an affirmative product match 28, field displays are enabled 34, basic fields are populated 36 and solution query 38 occurs as to whether the product is in the form of a solution. If so, solution normality is enabled and populated 40 and the size fields are populated 42 prior to entry into the CID number modified subroutine 32.

If the form query 38 is negative, i.e., the product is not a solution, the size fields are populated 42 prior to entry into the CID number modified subroutine 32.

Figure 3A:
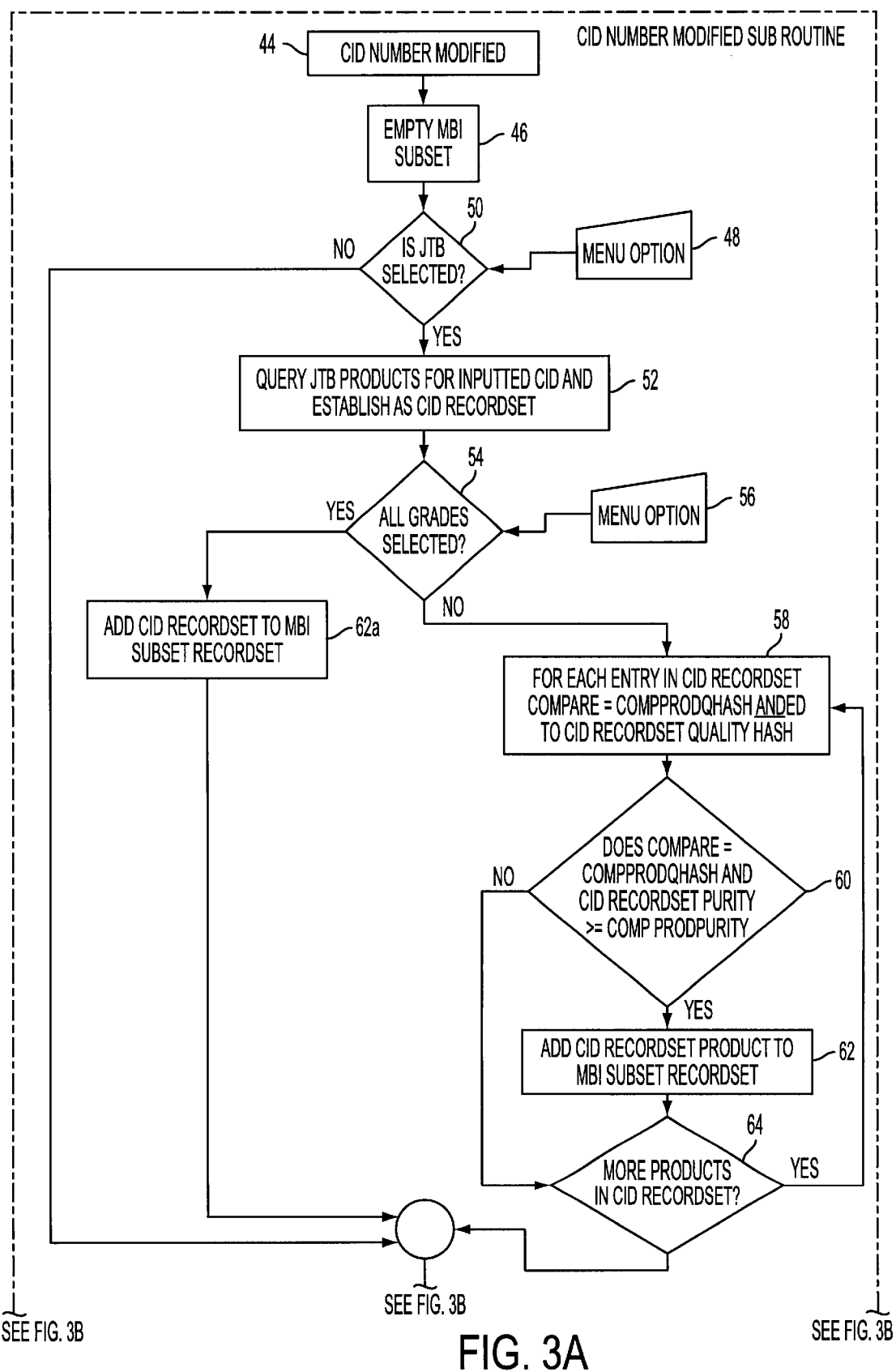
FIGS. 3A and 3B together form a block diagram showing a chemical identification number modified subroutine in accordance with one aspect of the present invention.
Figure 3B:
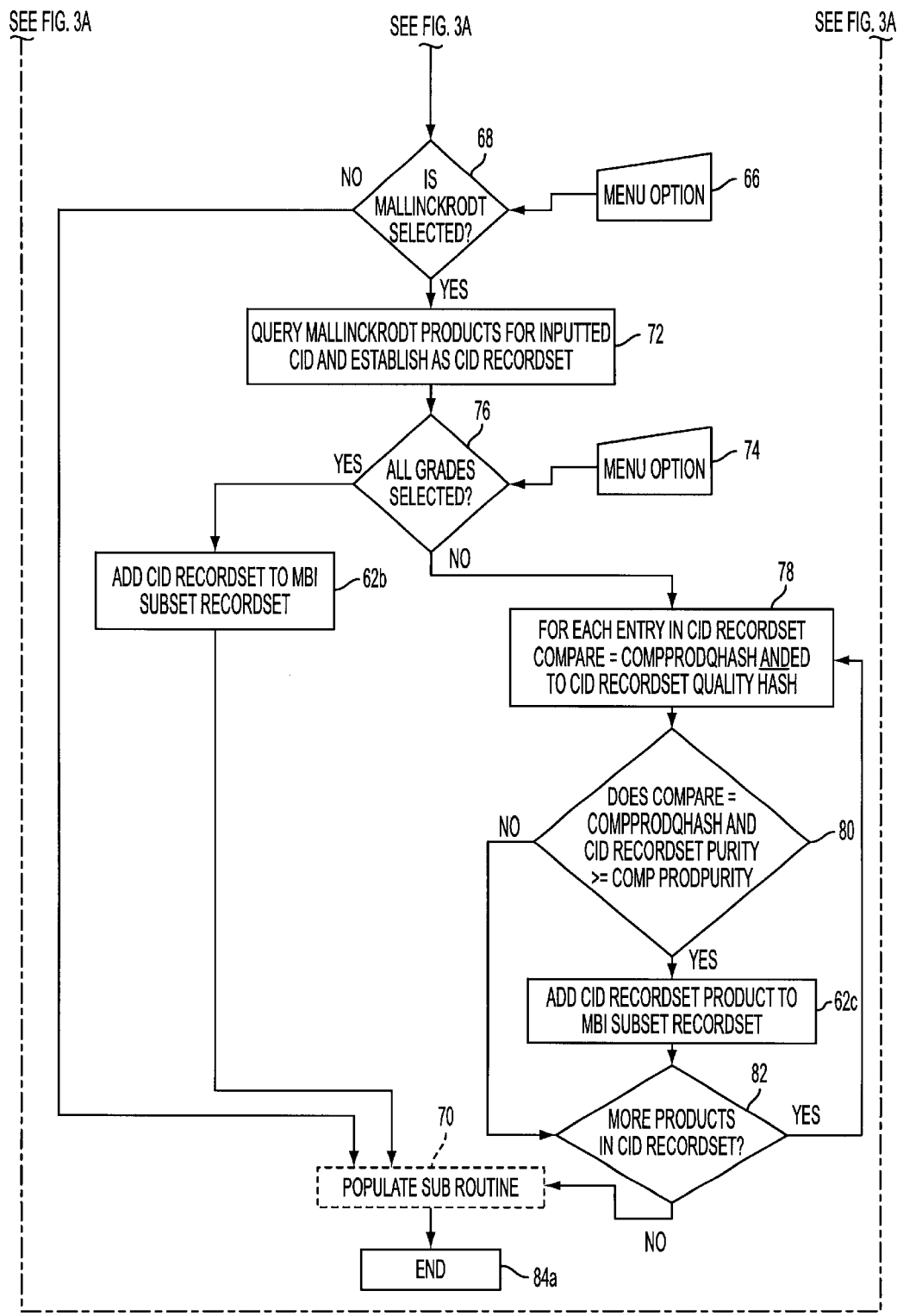

The CID number modified subroutine is described in more detail with respect to FIG. 3A. The terms MBI and JTB represent names of companies that produce chemical products. "Mallinckrodt" is a registered trademark of Mallinckrodt Inc., the assignee of this invention and a manufacturer of chemical products. The term "Comp" refers to one or more competitor companies.

As shown in FIG. 3A the CID number modified 44 empties the MBI products subset 46 and a menu option 48 is provided with a determination as to whether a JTB product is selected 50. If at step 50, a JTB product is not selected, menu option 66 is provided and a determination is made as to whether a Mallinckrodt® product is selected 68.

If a JTB product is selected, JTB products are queried for inputted CID and established as CID record set 52. A product grades menu option 56 is provided and a determination is made as to whether all grades are selected 54. If all grades are not selected at 54, for each entry into the CID record set a quality comparison 58 is made, as well as a purity comparison 60, which utilize both the specification type codes and the specification number codes for each entry. If the codes for the JTB product are not equal to or better than the codes for the inputted product at 58 and 60 a "no" response is generated at 60. With a no at 60 the CID record set is checked at 64. If there are additional JTB products in the record set to compare to the inputted product the program will loop back to 58 to perform these. If all of the products in the CID record set have been compared the program advances to 68. If a "yes" is generated from the comparisons at 58 and 60 the JTB product is added to the MBI subset record set 62 and the CID record set is checked at 64. If there are additional JTB products in the record set to compare to the inputted product the program will loop back to 58 to perform these. If all of the products in the CID record set have been compared the program advances to 68.

If no more products are in the CID record set, a menu option 66 is provided as to whether a Mallinckrodt product 68 is selected.

If all grades are selected at 54, the CID record set is added to the MBI subset record set 62a, and menu option 66 is provided, followed by a determination as to whether a Mallinckrodt® product is selected 68.

If no Mallinckrodt® product is selected at 68, the program goes to the populate subroutine 70 which is described in more detail below with respect to FIG. 4. If a Mallinckrodt® product is selected at 68, Mallinckrodt® products are queried for inputted CID and established as a CID record set 72.

A menu option 74 is provided and a determination is made as to whether all grades are selected 76. If all grades are selected 76, the CID record set is added to the MBI subset record set 62b and the program goes to the populate subroutine 70 further described below with respect to FIG. 4.

If all grades are not selected at 76, for each entry into the CID record set a quality comparison 78 is made, as well as a purity comparison 80, which utilize both the specification type codes and the specification number codes for each entry. If the codes for the Mallinckrodt product are not equal to or better than the codes for the inputted product at 78 and 80 a "no" response is generated at 80. With a no at 80 the CID record set is checked at 82. If there are additional Mallinckrodt products in the record set to compare to the inputted product the program will loop back to 78 to perform these. If all of the products in the CID record set have been compared the program advances to the Populate sub routine 70. If a "yes" is generated from the comparisons at 78 and 80 the Mallinckrodt product is added to the MBI subset record set 62c and the CID record set is checked at 82. If there are additional Mallinckrodt products in the record set to compare to the inputted product the program will loop back to 78 to perform these. If all of the products in the CID record set have been compared the program advances to the Populate sub routine 70.

Figure 4:
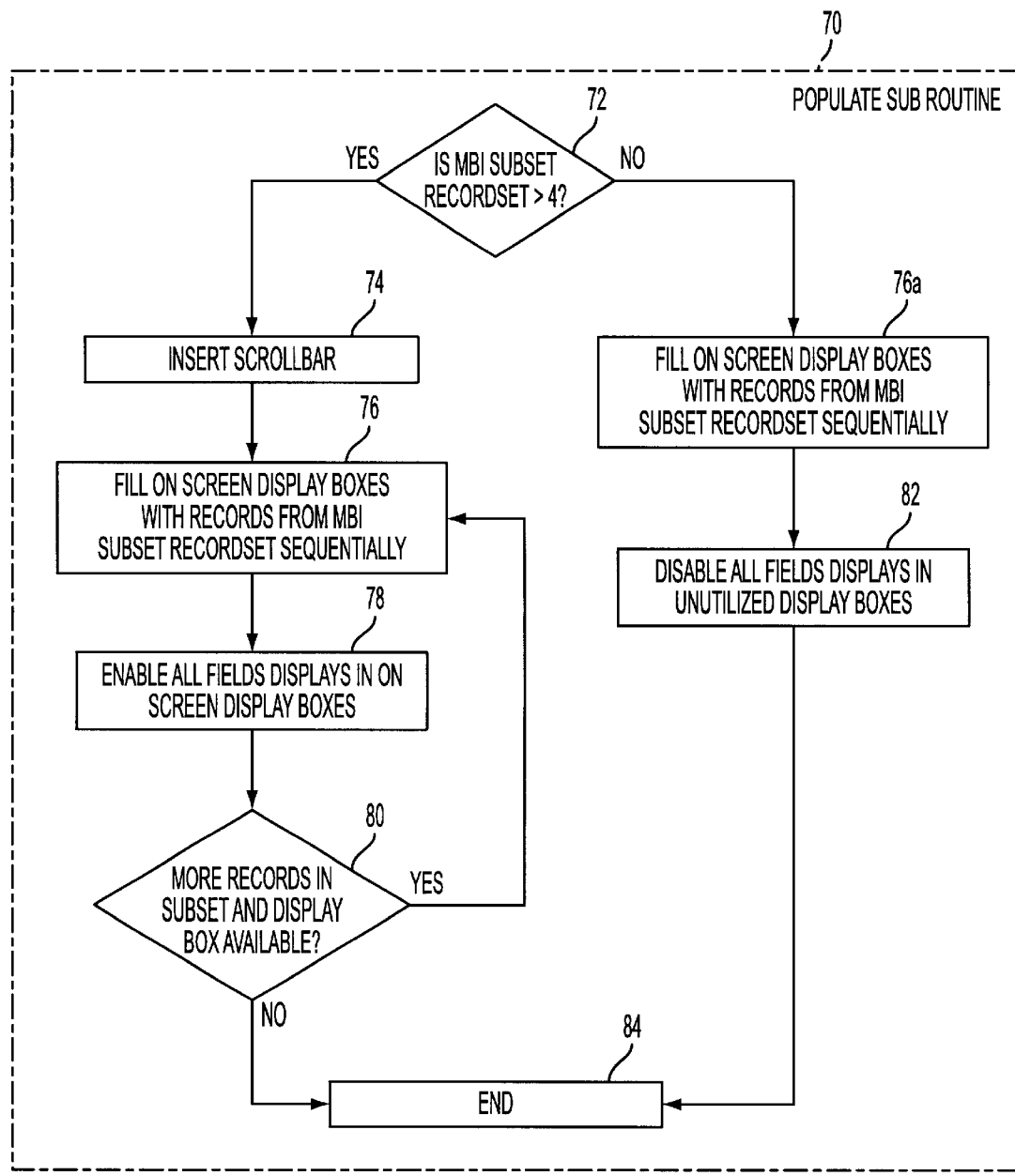
FIG. 4 is a block diagram showing a populate subroutine in accordance with one aspect of the present invention.

The populate subroutine 70 is shown in more detail in FIG. 4. In FIG. 4, a determination 72 is made as to whether the MBI subset record set is greater than 4. If so, the scroll bar is inserted 74 and the on screen display boxes are filled with records from the MBI subset record set sequentially 76, enable all fields displays in on screen display boxes 78 and a determination 80 is made as to whether more records in the subset and display box are available. If yes, the on screen display boxes are filled with records from the subset record set sequentially 76. If no, the program ends.

If the MBI subset record set 72 is less than or equal to 4, on screen display boxes are filled with records from the MBI subset record set sequentially 76a, and all fields displays in unutilized display boxes are disabled 82 prior to the program ending 84. This also is shown in FIG. 3C, wherein after the populate subroutine 70 the program ends 84a. Similarly, as shown in Fig. 1A, the program ends 26 after the CID number modified subroutine 32.

Figure 2:
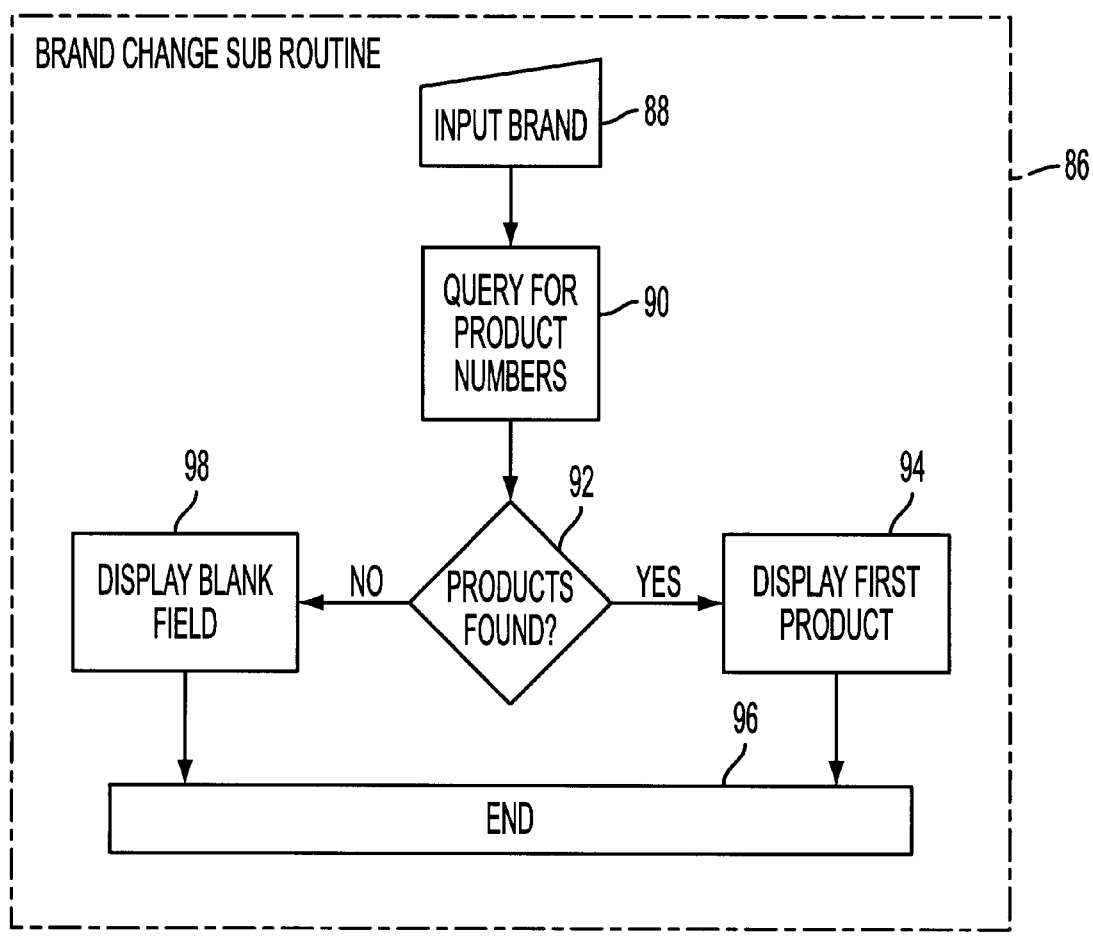
FIG. 2 is a block diagram showing a brand change subroutine in accordance with one aspect of the present invention.

The brand change subroutine 86 is shown in FIG. 2. In this subroutine, a brand is inputted 88 and a query 90 is made for product numbers. If one or more products 92 is found, products are displayed 94 prior to the program end 96. If products 92 are not found, a blank field is displayed 98 prior to the program end 96.

Figure 5A:
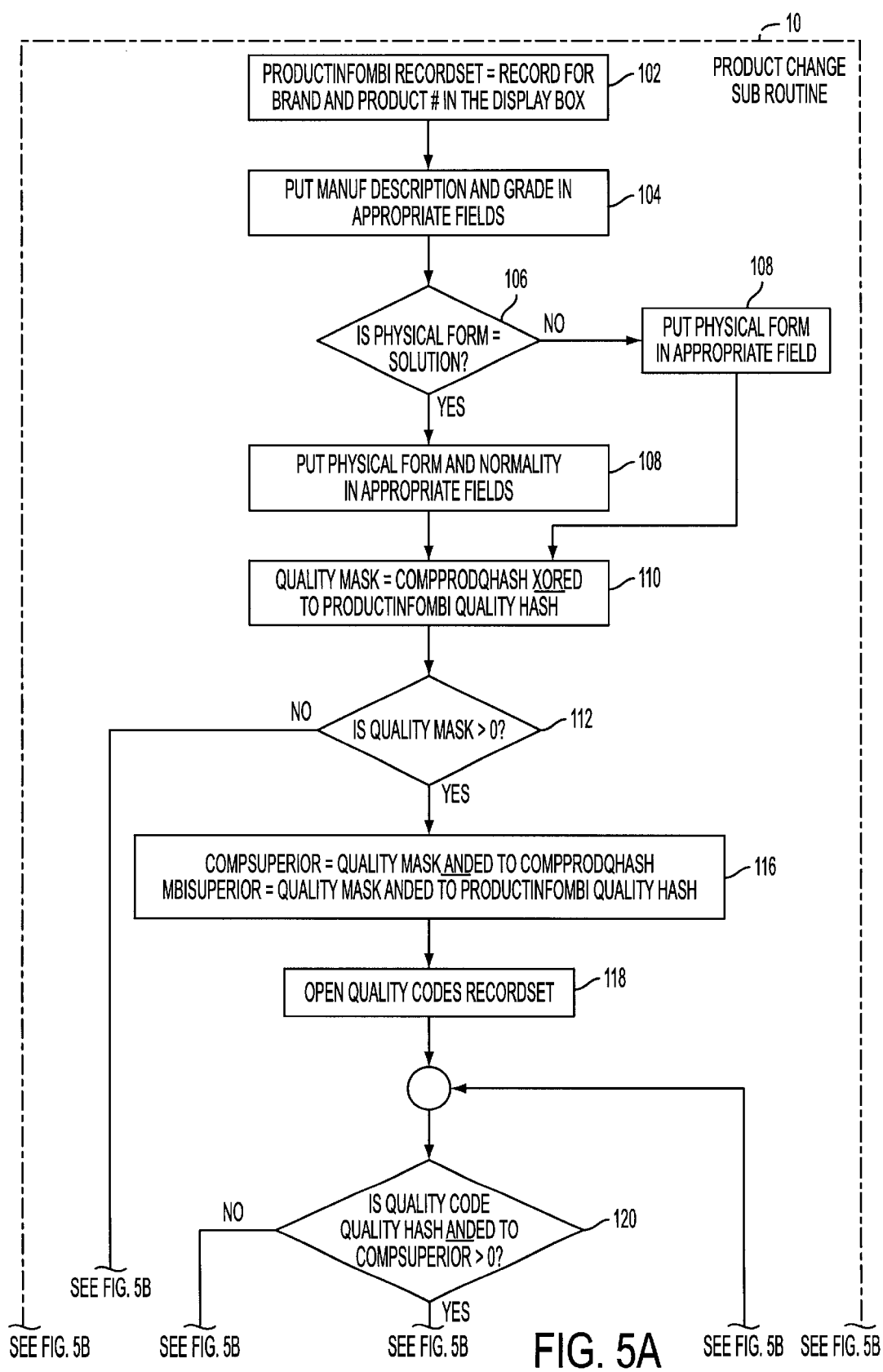
FIGS. 5A, 5B and 5C together form a block diagram showing a product change subroutine in accordance with one aspect of the present invention.
Figure 5B:
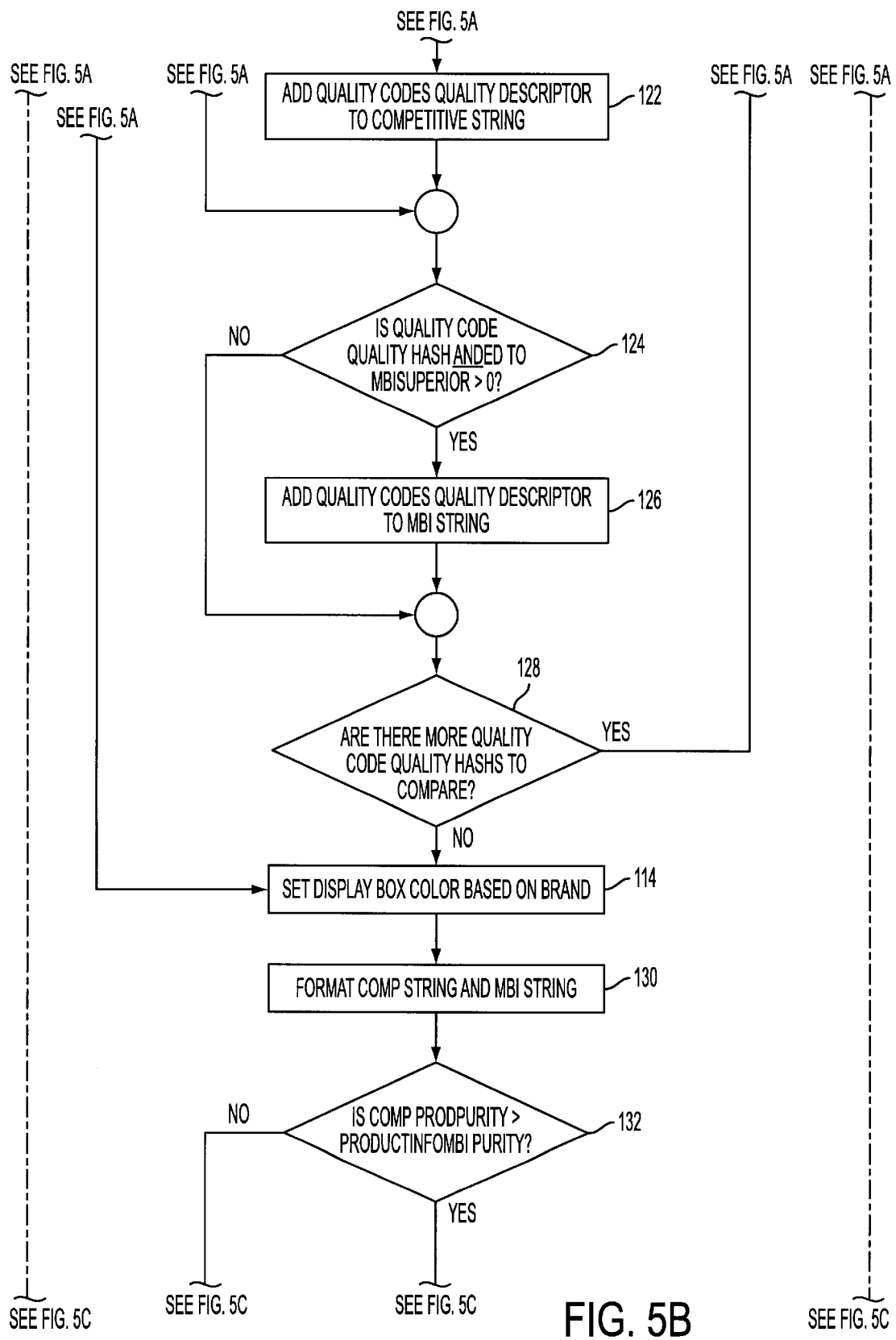
Figure 5C:
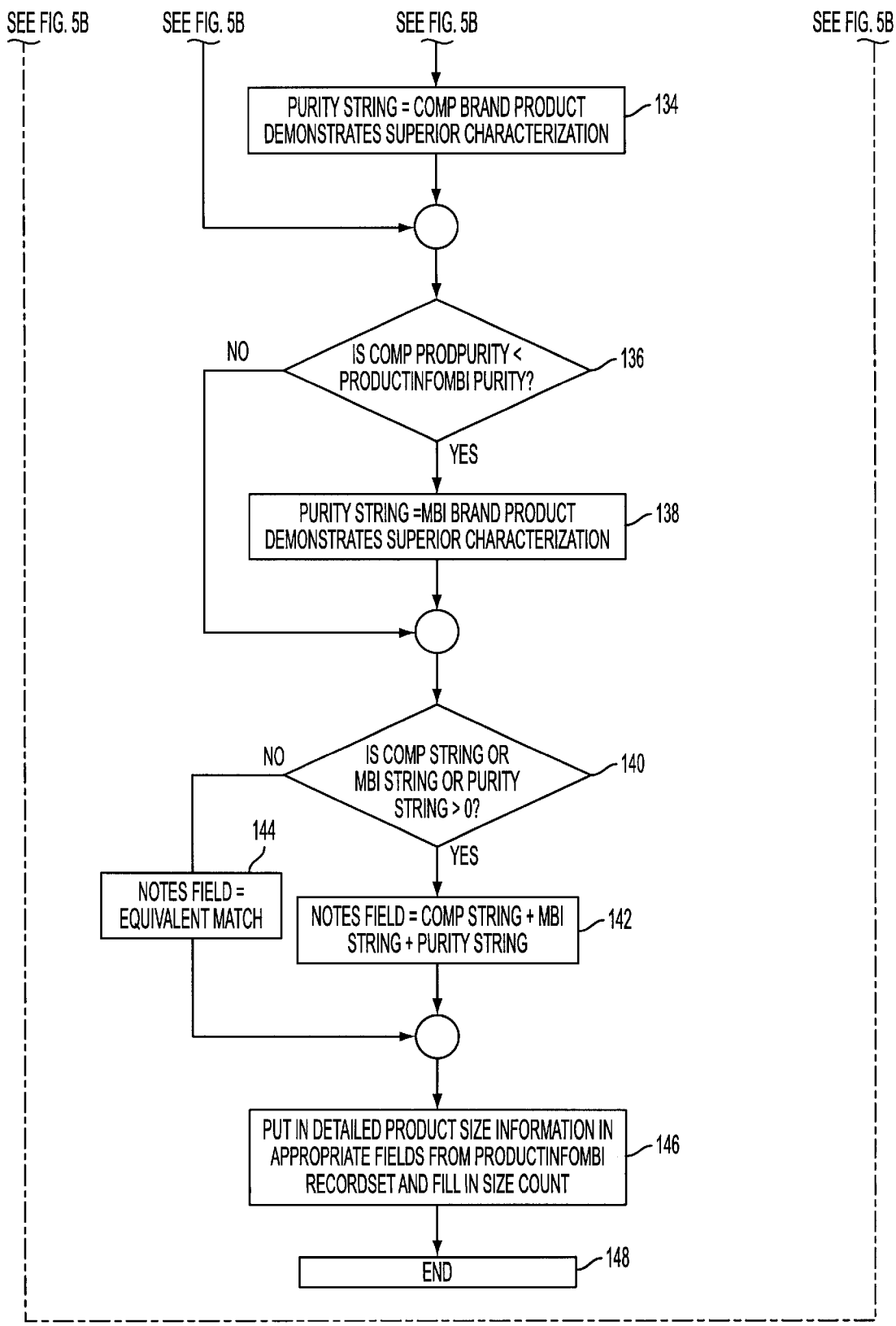

The product change subroutine 100 is further described with respect to FIG. 5A. With the complete record for the brand and product number in the display box 102 the manufacturer's description and grade is put into appropriate fields 104. A physical form query 106 is made, and if the product is a solution, the physical form and normality are put in appropriate fields 108 prior to a quality mask interpretation 110.

If the physical form 106 is not a solution, the physical form is put into an appropriate field 108 prior to the quality mask interpretation 110.

At 112, a determination is made as to whether the quality mask is greater than 0, meaning a unique quality code exists. That is, there is at least one unique property for one of the products being compared. If the quality mask is not greater than 0, the display box color based on brand is set 114 and the competitive product string and the MBI product string are equal to 0. At 116, the quality mask, if greater than 0, is used to determine which particular product contains the specific unique attribute. After these determinations are made at 116, the quality codes record set are opened at 118. For each additional product quality descriptors in the record set, a series of queries and answers 120, 122, 124, 126 and 128 are made in order to determine whether to assign a particular quality code descriptor as belonging to one of the products by adding it to one of either the competitive product string or MBI product string. At 114, the display box color based on brand.

The competitive product string and the MBI product string is formatted at 130, and a series of queries and answers 132, 134, 136, 138, 140 and 142 are made in the steps required for identification of an equivalent match 144. If both products have the same purity codes, i.e., number of specifications, then the purity codes are equal at 132 and 136 and the purity string equals 0. If the purity string, the competitive product string, and the MBI product string are all equal to zero at 140, then the two products are labelled equivalent matches at 144. Detailed product size information is inserted in 146 prior to ending of the program 148. If both products do not have the same purity codes at 132 and 136 then the product with the higher purity code is labeled with superior characterization at 134 or 138. If the strings from 134, 138 or 130 contain information at 140 then the Notes field at 142 is equal to the strings from 130, 134 and 138.

Figure 6A:
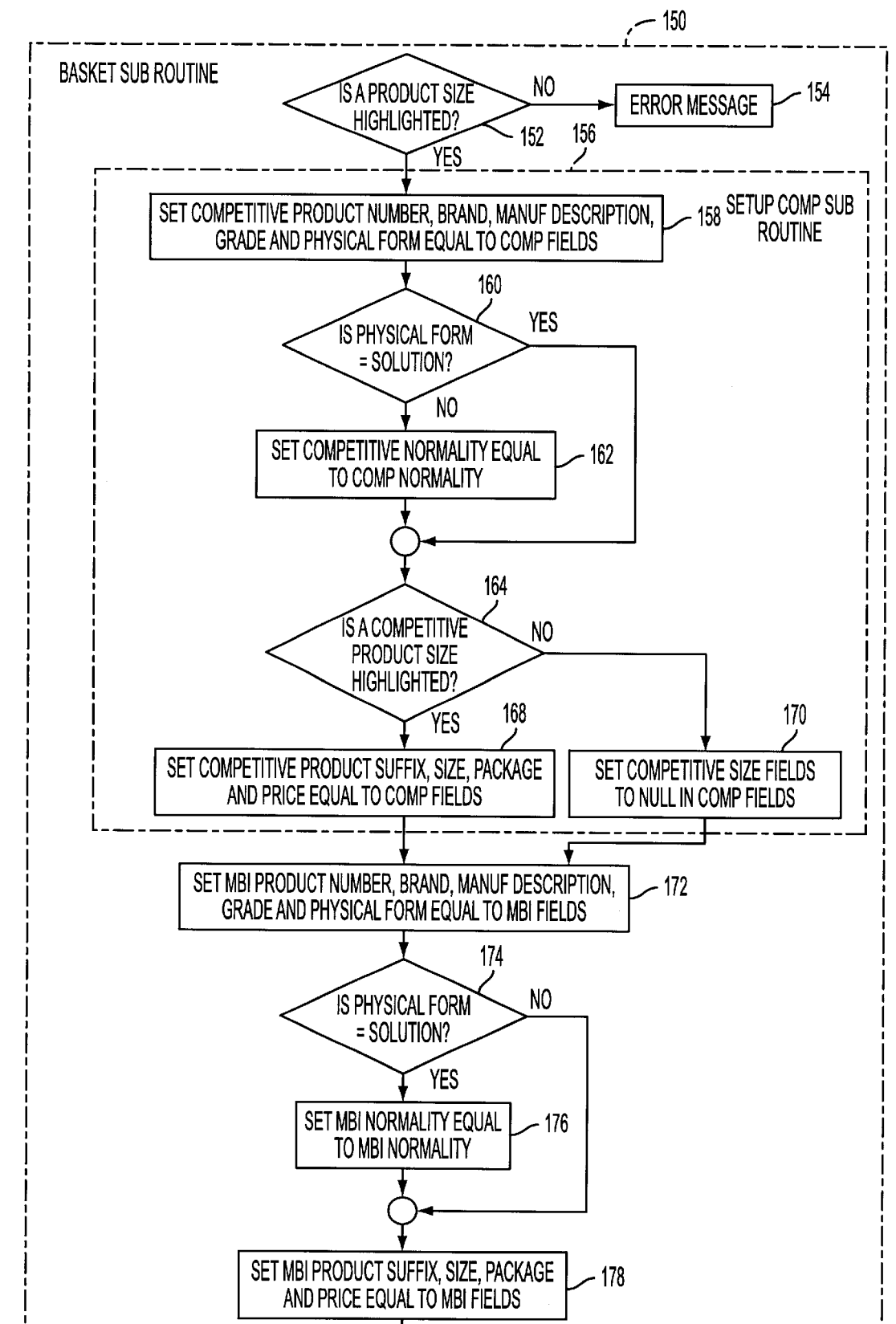
FIGS. 6A and 6B together form a block diagram showing a basket subroutine in accordance with one aspect of the present invention.
Figure 6B:
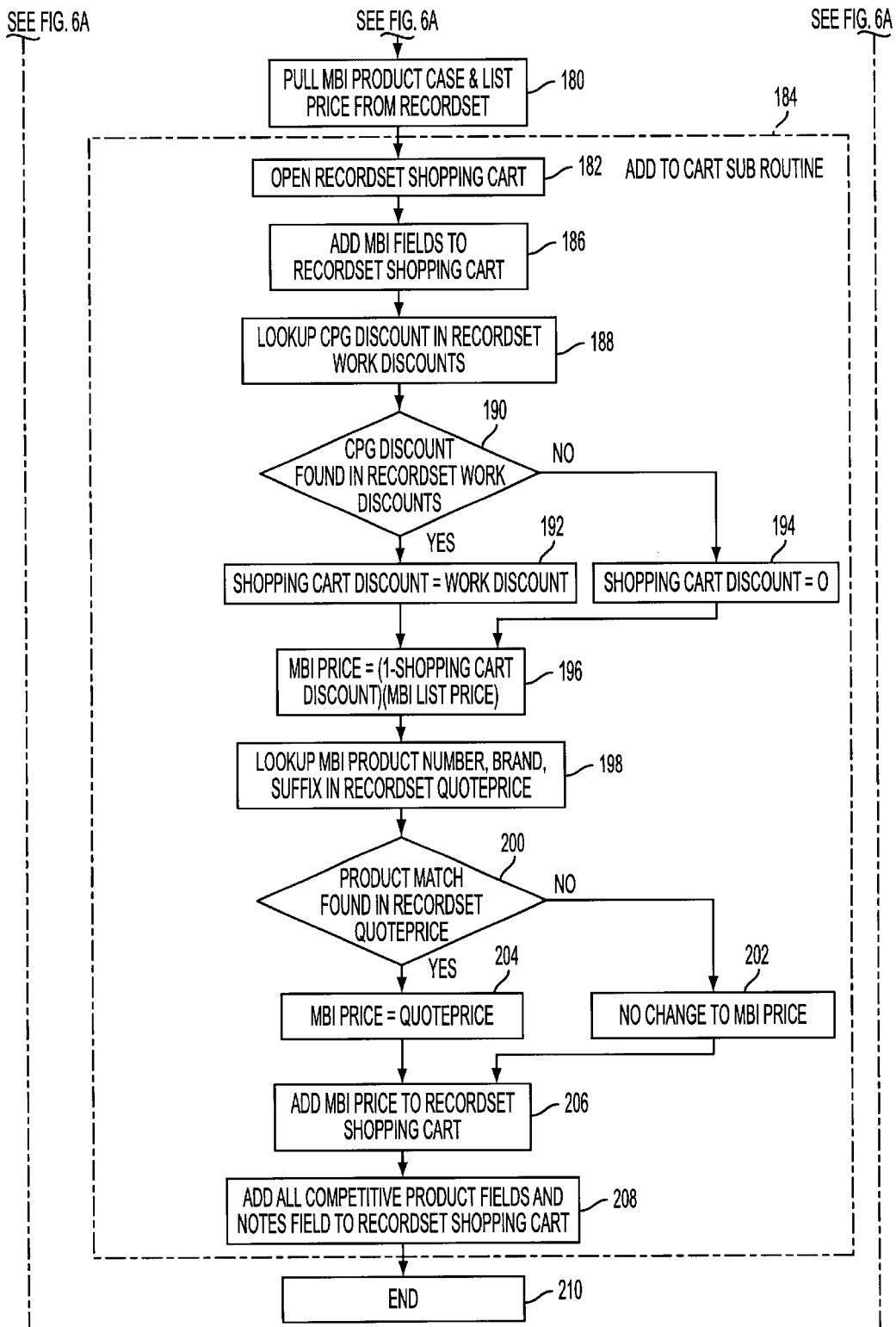

The basket subroutine 150 is illustrated in detail in FIG. 6A and 6B. In order for this subroutine to operate, a product size must be highlighted 152. If no product size is highlighted 152, an error message 154 results.

If a product size is highlighted 152, the set up Comp (competitive product) subroutine 156 is entered. Information on competitive products is set in 158 and various queries and answers 160, 162, 164, 168 and 170 take place prior to exiting the set up comp subroutine 156. Various MBI product information is set at 172. A series of queries and answers with respect to the MBI products takes place in steps 174, 176, 178 and 180 prior to opening the record set shopping cart 182 in the add to cart subroutine 184.

The MBI product fields are added to the record set shopping cart at 186 and product discounts are searched in 188. A series of discount and price comparisons is made in steps 190, 192, 194, 196, 200, 202 and 204, prior to the MBI price being added to the record set shopping cart at 206 and the competitive product fields being added to the record set shopping cart at 208 before the program is ended at 210.

The present invention is a system which provides accurate information in a quick and convenient format that will allow users to identify other products that will work in their application and weigh the attributes of the other products against those of the current product.

When the multi-code groups for different products are compared in accordance with the present invention, equal substance codes indicate that the products are chemically identical. A product having a higher specification number code is highlighted as having a higher degree of characterization. The invention uses the specification type code to highlight key differences between products, calculates product pricing, and is capable of providing multiple report formats.

Since many modifications, variations and changes in detail may be made to the described embodiments, it is intended that all matter in the foregoing description and shown in the accompanying drawings and microfiche appendix be interpreted as illustrative and not in a limiting sense.

What is claimed is:

1. A process for comparing a plurality of chemical products, comprising:
   A) providing a plurality of multi-code groups, each multi-code group corresponding to a separate product, each said multi-code group comprising:
      a substance code indicating a chemical substance identification of said product,
      a specification number code indicating a number of specifications characterizing said chemical substance, and
      if the number of specifications of a particular product is greater than zero, a specification type code indicating at least one type of specification characterizing said chemical substance, or at least one attribute of said chemical substance, or a combination thereof; and
   B) comparing said multi-code groups for different products so as to identify similarities and differences between different products based on similarities and differences between corresponding substance codes, specification number codes and specification type codes of said different products.

2. The process of claim 1 wherein each of said multi-code groups characterizes a corresponding chemical product.

3. The process of claim 2 wherein said specification type code indicates a plurality of specification types, a plurality of attributes of said chemical substance, or a combination thereof.

4. The process of claim 3, wherein said specification type code specifies a product characteristic selected from the group consisting of product purity, product moisture content, presence of preservative, presence of other ingredients, product sterility, suitable product uses, product compliance with established standards and combinations thereof, and wherein said comparing step comprises comparing corresponding characteristics of said different products to identify said similarities and differences between said different products.

5. The process of claim 4 further comprising characterizing each of said chemical products by features selected from the group consisting of manufacturer, manufacturer's product number, manufacturer's description, manufacturer's grade, manufacturer's package suffix, product trade name, product package size, product package description and combinations thereof.

6. The process of claim 5 further comprising characterizing each of said chemical products by list price, discount price or both.

7. The process of claim 1, further comprising forming a database for comparing said chemical products by entering a product name into said database, selecting said features and characteristics corresponding to said product name from a menu containing a plurality of said features and characteristics, and assigning a multi-code group to said product name corresponding to the selected features and characteristics.

8. An apparatus for carrying out the process of claim 1, comprising a data processing system including:
   A) a plurality of multi-code groups, each of said multi-code groups comprising:
      a substance code indicating a chemical substance identification of said product,
      a specification number code indicating a number of specifications characterizing said chemical substance, and
      if the number of specifications is greater than zero, a specification type code indicating at least one type of specification characterizing said chemical substance, or at least one attribute of said chemical substance or a combination thereof; and
   B) a comparer which compares said multi-code groups for different products so as to identify similarities and differences between different products based on similarities and differences between corresponding substance codes, specification number codes and specification type codes of said different products.

9. The apparatus of claim 8 wherein each of said multi-code groups characterizes a corresponding chemical product.

10. The apparatus of claim 8 wherein said specification type code indicates a plurality of specification types, a plurality of attributes of said chemical substance, or a combination thereof.

11. The apparatus of claim 8, wherein said specification type code specifies a product characteristic selected from the group consisting of product purity, product moisture content, physical form of product, presence of preservative, presence of other ingredients, product sterility, suitable product uses, product compliance with established standards and combinations thereof, and wherein said comparing step comprises comparing corresponding characteristics of said different products to identify said similarities and differences between said different products.

12. The apparatus of claim 8 wherein each of said chemical products is characterized by features selected from the group consisting of manufacturer, manufacturer's product number, manufacturer's description, manufacturer's grade, manufacturer's package suffix, product trade name, product package size, product package description and combinations thereof.

13. The apparatus of claim 8 wherein each of said chemical products is characterized by list price, discount price or both.

14. The apparatus of claim 8, further comprising a database for comparing said chemical products by entering a product name into said database, selecting said features and characteristics corresponding to said product name from a menu containing a plurality of said features and characteristics, and assigning a multi-code group to said product name corresponding to the selected features and characteristics.

15. A storage medium for carrying out the process of claim 1, including information capable of comparing chemical products, comprising:

A) processing devices for storing a plurality of multi-code groups, each of said multi-code groups comprising:
   a substance code indicating a chemical substance identification of said product,
   a specification number code indicating a number of specifications characterizing said chemical substance, and
   if the number of specifications is greater than zero, a specification type code indicating at least one type of specification characterizing said chemical substance, or at least one attribute of said chemical substance or a combination thereof; and B) a comparing device capable of comparing said multi-code groups for different products so as to identify similarities and differences between different products based on similarities and differences between corresponding substance codes, specification number codes and specification type codes of said different products.

16. The storage medium of claim 1 wherein each of said multi-code groups characterizes a corresponding chemical product.

17. The storage medium of claim 2 wherein said specification type code indicates a plurality of specification types, a plurality of attributes of said chemical substance, or a combination thereof.

18. The storage medium of claim 3, wherein said specification type code specifies a product characteristic selected from the group consisting of product purity, product moisture content, presence of preservative, presence of other ingredients, product sterility, suitable product uses, product compliance with established standards and combinations thereof, and wherein said comparing step comprises comparing corresponding characteristics of said different products to identify said similarities and differences between said different products.

19. The storage medium of claim 4 wherein each of said chemical products is characterized by features selected from the group consisting of manufacturer, manufacturer's product number, manufacturer's description, manufacturer's grade, manufacturer's package suffix, product trade name, product package size, product package description and combinations thereof.

20. The storage medium of claim 5 wherein each of said chemical products is characterized by list price, discount price or both.

21. The storage medium of claim 1, further comprising a database for comparing said chemical products by entering a product name into said database, selecting said features and characteristics corresponding to said product name from a menu containing a plurality of said features and characteristics, and assigning a multi-code group to said product name corresponding to the selected features and characteristics.

* * * * *